(12) United States Patent
Lin et al.

(10) Patent No.: US 12,203,131 B2
(45) Date of Patent: Jan. 21, 2025

(54) GENE SEQUENCING STRUCTURE, GENE SEQUENCING DEVICE AND GENE SEQUENCING METHOD

(71) Applicant: Shanghai Tianma Micro-Electronics Co., Ltd., Shanghai (CN)

(72) Inventors: Baiquan Lin, Shanghai (CN); Kerui Xi, Shanghai (CN); Kaidi Zhang, Shanghai (CN); Wei Li, Shanghai (CN); Yunfei Bai, Shanghai (CN); Ping Su, Shanghai (CN); Junting Ouyang, Shanghai (CN)

(73) Assignee: Shanghai Tianma Micro-Electronics Co., Ltd., Shanghai (CN)

( * ) Notice: Subject to any disclaimer, the term of this patent is extended or adjusted under 35 U.S.C. 154(b) by 530 days.

(21) Appl. No.: 17/580,176

(22) Filed: Jan. 20, 2022

(65) Prior Publication Data
US 2023/0151408 A1    May 18, 2023

(30) Foreign Application Priority Data
Nov. 18, 2021   (CN) .......................... 202111366541.2

(51) Int. Cl.
C12Q 1/00      (2006.01)
B01L 3/00      (2006.01)
C12Q 1/6825    (2018.01)
G01N 27/414    (2006.01)

(52) U.S. Cl.
CPC ....... C12Q 1/6825 (2013.01); G01N 27/4145 (2013.01)

(58) Field of Classification Search
CPC .......................... C12Q 1/6825; G01N 27/4145
See application file for complete search history.

(56) References Cited

U.S. PATENT DOCUMENTS

| 2010/0270174 | A1* | 10/2010 | Chen ................ G01N 33/54313 205/792 |
| 2019/0025242 | A1  | 1/2019  | Pang et al. |
| 2020/0299765 | A1* | 9/2020  | Cai ...................... C12Q 1/6874 |
| 2023/0408510 | A1* | 12/2023 | Goldsmith ......... G01N 27/4145 |

FOREIGN PATENT DOCUMENTS

| CN | 109266727 A | 1/2019 |
| CN | 106782239 B | 4/2020 |
| CN | 211428122 U | 9/2020 |

* cited by examiner

*Primary Examiner* — Nathan A Bowers
(74) *Attorney, Agent, or Firm* — Anova Law Group, PLLC

(57) ABSTRACT

A gene sequencing structure, a gene sequencing device and a gene sequencing method are provided. The gene sequencing structure includes a substrate, a thin-film transistor array layer located on the substrate and including thin-film transistors that include a first electrode, and a second electrode; an ion-sensitive layer located on a side of the semiconductor layer away from the substrate; a micro-hole layer located on a side of the ion-sensitive layer away from the substrate, including a through-hole passing through the micro-hole layer, at least partially overlapping the semiconductor layer, and used for receiving a to-be-tested single-stranded nucleic acid inside; a conductive structure, located on a side of the layer away from the substrate and electrically connected to the first electrode or the second electrode; and a detection chip, located on a side of the conductive structure away from the substrate and electrically connected to the conductive structure.

17 Claims, 6 Drawing Sheets

GENE SEQUENCING STRUCTURE, GENE SEQUENCING DEVICE AND GENE SEQUENCING METHOD

CROSS-REFERENCE TO RELATED APPLICATION

This application claims the priority of Chinese Patent Application No. 202111366541.2, filed on Nov. 18, 2021, the content of which is incorporated by reference in its entirety.

TECHNICAL FIELD

The present disclosure generally relates to the field of gene sequencing and bio-detection and, more particularly, relates to a gene sequencing structure, a gene sequence device, and a gene sequencing method.

BACKGROUND

Gene sequencing technology is a type of gene detection technology, which is the widely used in modern molecular biology research. Gene sequencing can analyze and determine the complete sequence of genes from blood or saliva to predict the possibility of suffering from a variety of diseases, such as cancer or leukemia.

Gene sequencing technologies mainly include the sequencing-by-synthesis technology, the ion-semiconductor sequencing technology, and the ligation sequencing technology, etc. Among them, the sequencing-by-synthesis technology is the mainstream, and occupies a leading position in the market. The sequencing-by-synthesis technology is to label four different deoxyribonucleotides with different colors of fluorescence (the four deoxyribonucleotides contain A adenine, T thymine, C cytosine, and G guanine). When a DNA polymerase synthesizes the complementary strand, each addition of a deoxyribonucleotide will release a different fluorescence. According to the captured fluorescence signal and processed by a specific a computer software, the sequence information of the to-be-tested DNA can be obtained.

At present, the existing fluorescence detection scheme requires a complicated laser light source and optical system, which complicates the sequencing system. In addition, labeling chemical reagents are extremely expensive, resulting in a high sequencing cost. Therefore, there is an urgent need for a gene sequencing to solve one or more problems set forth above and other problems in the arts.

SUMMARY

One aspect of the present disclosure provides a gene sequencing structure. The gene sequencing structure includes a substrate and a thin-film transistor array layer located on a side of the substrate. The thin-film transistor array layer includes a plurality of thin-film transistors, each of the plurality of thin-film transistors includes a first electrode, a second electrode, a third electrode, and a semiconductor layer, the first electrode and the second electrode are spaced apart and located in a same layer, the semiconductor layer is located on a side of the first electrode and the second electrode adjacent to the substrate, the semiconductor layer at least partially overlaps the first electrode and the second electrode, respectively, the semiconductor layer at least partially overlaps the third electrode, and an insulation layer is disposed between the semiconductor layer and the third electrode. The gene sequencing structure also includes an ion-sensitive layer located on a side of the semiconductor layer away from the substrate; and a micro-hole layer, located on a side of the ion-sensitive layer away from the substrate. The micro-hole layer includes a through-hole, the through-hole passes through the micro-hole layer in a direction perpendicular to the substrate, the through-hole at least partially overlaps the semiconductor layer, and the through-hole is used for receiving a to-be-tested single-stranded nucleic acid inside. Further, the gene sequencing structure includes a conductive structure located on a side of the layer away from the substrate, and electrically connected to the first electrode or the second electrode; and a detection chip, located on a side of the conductive structure away from the substrate, and electrically connected to the conductive structure.

Another aspect of the present disclosure provides a gene sequencing device. The gene sequencing device include a plurality of gene sequencing structures. Each gene sequencing structure includes a substrate and a thin-film transistor array layer located on one side of the substrate. The thin-film transistor array layer includes a plurality of thin-film transistors, each of the plurality of thin-film transistors includes a first electrode, a second electrode, a third electrode, and a semiconductor layer, the first electrode and the second electrode are spaced apart and located in a same layer, the semiconductor layer is located on a side of the first electrode and the second electrode adjacent to the substrate, the semiconductor layer at least partially overlaps the first electrode and the second electrode, respectively, the semiconductor layer at least partially overlaps the third electrode, and an insulation layer is disposed between the semiconductor layer and the third electrode. The gene sequencing structure also includes an ion-sensitive layer located on a side of the semiconductor layer away from the substrate; and a micro-hole layer, located on a side of the ion-sensitive layer away from the substrate. The micro-hole layer includes a through-hole, the through-hole passes through the micro-hole layer in a direction perpendicular to the substrate, the through-hole at least partially overlaps the semiconductor layer, and the through-hole is used for receiving a to-be-tested single-stranded nucleic acid inside. Further, the gene sequencing structure includes a conductive structure located on a side of the layer away from the substrate, and electrically connected to the first electrode or the second electrode; and a detection chip, located on a side of the conductive structure away from the substrate, and electrically connected to the conductive structure.

Another aspect of the present disclosure includes providing a gene sequencing method. The gene sequencing method includes providing a gene sequencing structure. The gene sequencing structure includes a substrate and a thin-film transistor array layer located on a side of the substrate. The thin-film transistor array layer includes a plurality of thin-film transistors, each of the plurality of thin-film transistors includes a first electrode, a second electrode, a third electrode, and a semiconductor layer, the first electrode and the second electrode are spaced apart and located in a same layer, the semiconductor layer is located on a side of the first electrode and the second electrode adjacent to the substrate, the semiconductor layer at least partially overlaps the first electrode and the second electrode, respectively, the semiconductor layer at least partially overlaps the third electrode, and an insulation layer is disposed between the semiconductor layer and the third electrode. The gene sequencing structure also includes an ion-sensitive layer located on a side of the semiconductor layer away from the substrate; and a micro-hole layer, located on a side of the ion-sensitive layer away from the substrate. The micro-hole layer includes a through-hole, the through-hole passes through the micro-hole layer in a direction perpendicular to the substrate, the through-hole at least partially overlaps the semiconductor layer, and the through-hole is used for placing a to-be-tested single-stranded nucleic acid inside. Further, the gene sequencing structure includes a conductive structure located on a side of the layer away from the substrate, and electrically connected to the first electrode or the second electrode; and a detection chip, located on a side of the conductive structure away from the substrate, and electrically connected to the conductive structure. The gene sequencing method also includes placing the to-be-tested single-stranded nucleic acid in the through-hole by contacting with the ion-sensitive layer; applying a first voltage signal to the first electrode or the second electrode, and applying a second voltage signal to the third electrode; passing four kinds of deoxyribonucleotides into the through-hole in sequence; detecting whether a current is generated between the first electrode and the second electrode through the conductive structure electrically connected to the detection chip using the detection chip to determine a base type of the to-be-tested single-stranded nucleic acid according to the deoxyribonucleotide introduced therein as the current is generated; and neutralizing and processing a reagent in the through-hole to restore the thin-film transistor to an initial state after each type of deoxyribonucleic acid is passed into the through-hole. The initial state is that the detection chip cannot detect a current generated between the first electrode and the second electrode. Further, the gene sequencing method includes eluting the reagent in the through-hole after the detection of each site of multiple to-be-tested single-stranded nucleic acids is completed.

Other aspects of the present disclosure can be understood by those skilled in the art in light of the description, the claims, and the drawings of the present disclosure.

BRIEF DESCRIPTION OF THE DRAWINGS

The drawings incorporated in the specification and constituting a part of the specification illustrate the embodiments of the present disclosure, and together with the description are used to explain the principle of the present disclosure.

DETAILED DESCRIPTION

To make the objectives, technical solutions, and advantages of the present disclosure clearer, the following further describes the present disclosure in detail with reference to the accompanying drawings and embodiments. It should be understood that the specific embodiments described here are only used to explain the present disclosure, and are not used to limit the present disclosure.

When certain words are used in the specification and claims to refer to specific components, those skilled in the art should understand that hardware manufacturers may use different terms to refer to the same component. This specification and claims do not use differences in names as a way of distinguishing components, but use differences in functions of components as a criterion for distinguishing. If "include" mentioned in the entire specification and claims is an open term, it should be interpreted as "include but not limited to". "Approximately" means that within an acceptable error range, those skilled in the art can solve the technical problem within a certain error range, and basically achieve the technical effect. In addition, the term "coupled" herein includes any direct and indirect electrical coupling means.

Therefore, if it is described in the text that a first device is coupled to a second device, it may mean that the first device can be directly electrically coupled to the second device, or indirectly electrically coupled to the second device through other devices or coupling means. The following description of the specification is a preferred embodiment for implementing the application, but the description is for the purpose of explaining the general principles of the application and is not intended to limit the scope of the application. The scope of protection of this application shall be subject to those defined by the appended claims. Among them, the similarities between the embodiments will not be repeated one by one.

The present disclosure provides a gene sequencing structure, a gene sequencing device, and a gene sequencing method.

Figure 1:
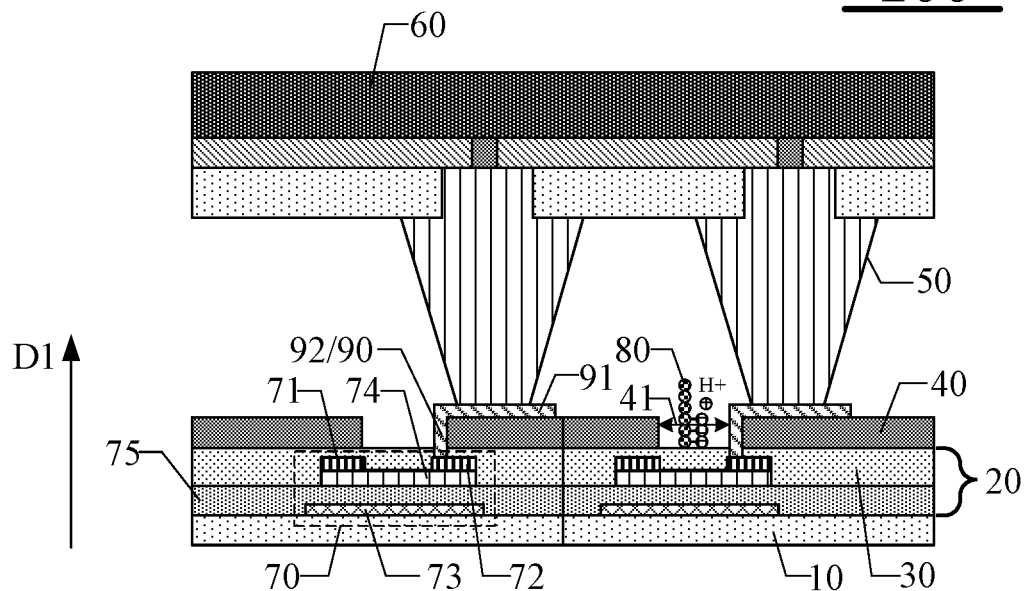
FIG. 1 illustrates a cross-sectional view of an exemplary gene sequencing structure according to various disclosed embodiments of the present disclosure.
Figure 2:
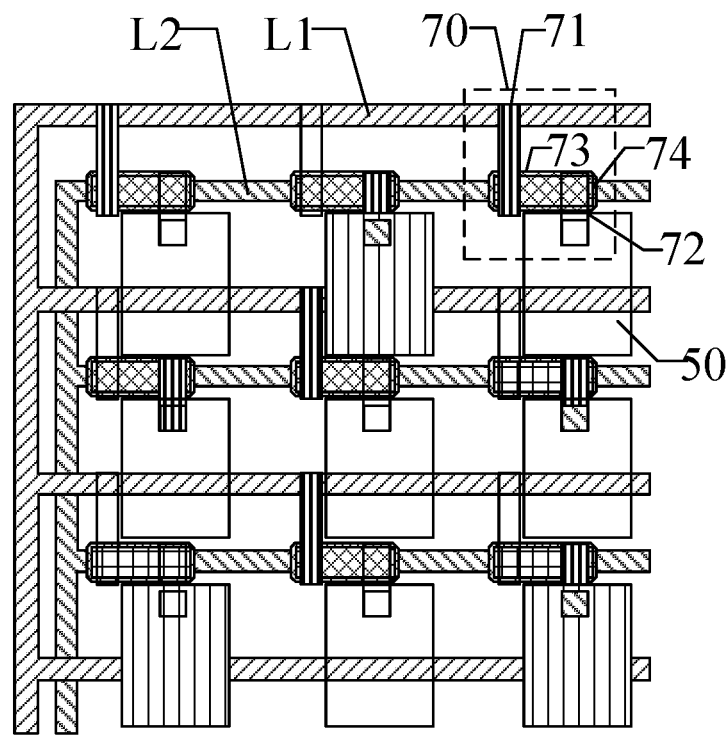
FIG. 2 illustrates a top view of an exemplary gene sequencing structure according to various disclosed embodiments of the present disclosure.

FIG. 1 illustrates a cross-sectional view of an exemplary gene sequencing structure according to various disclosed embodiments of the present disclosure, and FIG. 2 illustrates a top view of an exemplary gene sequencing structure according to various disclosed embodiments of the present disclosure.

As shown in FIGS. 1-2, a gene sequencing structure 100 may include a substrate 10 and a thin-film transistor array layer 20. The thin-film transistor array layer 20 may be located on one side of the substrate 10 and may include a plurality of thin-film transistors 70. A thin-film transistor 70 may include a first electrode 71, a second electrode 72, a third electrode 73, and a semiconductor layer 74. The first electrode 71 and the second electrode 72 may be spaced apart and may be disposed in a same layer. The semiconductor layer 74 may be disposed on a side of the first electrode 71 and the second electrode 72 adjacent to the substrate 10, and the semiconductor layer 74 may at least partially overlap the first electrode 71 and the second electrode 72, respectively. The semiconductor layer 74 and the third electrode 73 may at least partially overlap, and an insulation layer 75 may be disposed between the semiconductor layer 74 and the third electrode 73.

Further, the gene sequencing structure 100 may include an ion-sensitive layer 30. The ion sensitive layer 30 may be located on a side of the semiconductor layer 74 away from the substrate 10.

Further, the gene sequencing structure 100 may include a micro-hole layer 40. The micro-hole layer 40 may be located on a side of the ion-sensitive layer 30 away from the substrate 10. The micro-hole layer 40 may include a through-hole 41. In the direction D1 perpendicular to the substrate 10, the through-hole 41 may pass through the micro-hole layer 40, and the through-hole 41 may at least partially overlap the semiconductor layer 74. The to-be-tested single-stranded nucleic acid 80 may be placed in the through-hole 41.

Further, the gene sequencing structure 100 may include a conductive structure 50. The conductive structure 50 may be located on a side of the micro-hole layer 40 away from the substrate 10, and the conductive structure 50 may be electrically connected to the first electrode 71 or the second electrode 72.

Further, the gene sequencing structure 100 may include a detection chip 60. The detection chip 60 may be located on a side of the conductive structure 50 away from the substrate 10, and may be electrically connected to the conductive structure 50.

The gene sequencing structure in this embodiment may be configured to detect a gene sequence. For example, it may be configured to determine the types of bases of a set of to-be-tested single-stranded nucleic acids. Specifically, the conductive properties of the semiconductor layer in the thin-film transistor may be used to generate a current. Then, the unknown gene sequences may be determined through the detection of the detection chip.

Referring to FIG. 1 and FIG. 2, the gene sequencing structure 100 may be entirely disposed on the substrate 10. The substrate 10 may be configured as a carrier to carry other structures of the gene sequencing structure 100. The substrate 10 may be a glass substrate, or a flexible substrate, which is not limited in this embodiment. The thin-film transistor array layer 20 disposed on one side of the substrate 10 may include the plurality of thin-film transistors 70.

The thin-film transistor 70 may include the first electrode 71, the second electrode 72, the third electrode 73, and the semiconductor layer 74. In one embodiment, the first electrode 71 and the second electrode 72 may be source/drain metal layers, the third electrode 73 may be a gate metal layer, and the semiconductor layer 74 may be an active semiconductor layer. The first electrode 71 and the second electrode 72 may be arranged oppositely and spaced apart and located in the same layer. The semiconductor layer 74 may be located on the side of the first electrode 71 and the second electrode 72 adjacent to the substrate 10. Along the direction D1 perpendicular to the substrate 10, the semiconductor layer 74 may at least partially overlap the first electrode 71 and the second electrode 72, respectively. The insulation layer 75 may be disposed between the semiconductor layer 74 and the third electrode 73, and along the direction D1 perpendicular to the substrate 10, the orthographic projections of the semiconductor layer 74 and the third electrode 73 on the substrate 10 may at least partially overlap. The thin-film transistor 70 provided in this embodiment may be configured to transmit a gene detection signal.

Further, an ion-sensitive layer 30 may be disposed on the side of the semiconductor layer 74 away from the substrate 10. In one embodiment, the ion-sensitive layer 30 may include at least a sensitive material that can change the voltage of the ions generated by a base pairing. Accordingly, the ion-sensitive layer 30 in such an embodiment may need to be in contact with ions generated by the base pairing on the to-be-tested single-stranded nucleic acid 80. In addition, the ion-sensitive layer 30 may also need to be in contact with the semiconductor layer 74. The semiconductor layer 74 may be disposed in the ion-sensitive layer 30. Accordingly, when the base pairing on the to-be-tested single-stranded nucleic acid 80 generates ions, the electric potential above the thin-film transistor 70 may be changed, and the conductivity of the semiconductor layer 74 may be changed.

Further, the micro-hole layer 40 may be disposed on the side of the ion-sensitive layer 30 away from the substrate 10. The micro-hole layer 40 may include a plurality of through-holes 41, and the through-holes 41 may pass through the micro-hole layer 40, and the through-holes 41 may expose the ion-sensitive layer 30. Along the direction D1 perpendicular to the substrate 10, the through-holes 41 and the semiconductor layer 74 may at least partially overlap. The through-holes 41 may be configured to host the to-be-tested single-stranded nucleic acid 80 to provide a certain amount of space for the base pairing of the to-be-tested single-stranded nucleic acid 80.

It can be understood that, referring to FIG. 2, in one embodiment, a first voltage signal may be input to the first electrode 71 through the first metal wiring L1, and a second voltage signal may be input to the third electrode 73 through the second metal wiring L2. The signals may cause the surface of the semiconductor layer 74 to generate induced charges. As the first voltage signal input to the first electrode 71 changes, more induced charges may be generated on the surface of the semiconductor layer 74. When the number of the induced charges generated on the surface of the semiconductor layer 74 reaches a certain level, a carrier transport channel may be formed between the first electrode 71 and the second electrode 72. For example, a current may be generated between the first electrode 71 and the second electrode 72. During the entire gene sequencing process, the thin-film transistor 70 may be operated in a linear region. Further, when different deoxyribonucleotides are sequentially injected into the through-holes 41 of the micro-hole layer 40 and paired with the bases of the to-be-tested single-strand nucleic acids 80, hydrogen ions may be generated. The hydrogen ions may cause the potential above the thin-film transistor 70 to change, and the induced charges of the semiconductor layer 74 may be increased through the ion-sensitive layer 30. Further, the current between the first electrode 71 and the second electrode 72 may be increased. By monitoring the change of the current between the first electrode 71 and the second electrode 72, whether the base of the to-be-tested single-stranded nucleic acid 80 is paired may be determined, and the type of the base of the to-be-tested single-stranded nucleic acid 80 may also be determined. Comparing with the existing gene sequencing structure, the gene sequencing structure in this embodiment may adapt the existing thin-film transistor manufacturing process, and the base of the to-be-tested single-stranded nucleic acid may not require a fluorescent label and may not require a laser light source and optical system. In addition, the gene sequencing structure in this embodiment may add the signal control of the third electrode 73, which may make the thin-film transistor 70 to be operated in the linear region such that the current change detection between the first electrode 71 and the second electrode 72 may be more obvious.

Further, referring to FIG. 1 and FIG. 2, the conductive structure 50 may be disposed on the side of the micro-hole layer 40 away from the substrate 10, and the detection chip 60 may be disposed on the side of the conductive structure 50 away from the substrate 10. One end of the conductive structure 50 may be electrically connected to the second electrode 72, and the other end of the conductive structure 50 may be electrically connected to the detection chip 60. The detection chip 60 may detect the current change generated between the first electrode 71 and the second electrode 72 through the conductive structure 50. On the one hand, by introducing the conductive structure 50, the detection positions of the thin-film transistor 70 may be effectively increased, and the experimental efficiency may be effectively improved. On the other hand, the detection chip 60 may be disposed on the side of the conductive structure 50 away from the substrate 10, which may effectively save space of the side of the conductive structure 50.

It should be noted that the embodiment shown in FIG. 1 only schematically shows a schematic diagram of the conductive structure 50 being electrically connected to the thin-film transistor 70 and the detection chip 60, respectively, and may not represent the actual size of the conductive structure 50. Further, FIG. 1 only shows a form in which two adjacent gene detection structures are arranged side by side. Further, the embodiment shown in FIG. 1 only schematically shows one shape of the conductive structure 50, the conductive structure 50 may also have other shapes, which is not limited in this disclosure. The embodiment shown in FIG. 2 only schematically shows the positional relationship between the first electrode 71, the second electrode 72, the third electrode 73, the semiconductor layer 74, and the conductive structure 50, and may not represent the actual sizes.

Further, referring to FIG. 1, in one embodiment of the present disclosure, the gene sequencing structure may further include an output detection terminal 90. The output detection terminal 90 may be disposed between the conductive structure 50 and the first electrode 71 or the second electrode 72. The conductive structure 50 may be electrically connected with the first electrode 71 or the second electrode 72 through the output detection terminal 90.

For example, referring to FIGS. 1-2, the gene sequencing structure 100 in this embodiment may include the output detection terminal 90. The output detection terminal 90 may be disposed between the conductive structure 50 and the first electrode 71 or the second electrode 72. The output detection terminal 90 may match the size and shape of the conductive structure 50 without affecting the characteristics of the thin-film transistor 70. Further, the output detection terminal 90 may be selected to have a material different from the first electrode 71 or the second electrode 71 of the thin-film transistor 70. For example, the output detection terminal 90 may be made of a material with a better corrosion resistance to protect the thin-film transistor 70. In one embodiment, when the first electrode 71 is configured to input the first voltage signal, the output detection terminal 90 may be electrically connected to the second electrode 72 and the conductive structure 50, respectively. When the second electrode 72 is configured to input the first voltage signal, the output detection terminal 90 may be electrically connected to the first electrode 71 and the conductive structure 50, respectively. As shown in FIG. 1, the output detection terminal 90 may be electrically connected to the second electrode 72; and the first voltage signal may input by the first electrode 71 through the first metal wiring L1. In such a way, the detection chip 60 may detect the current change between the first electrode 71 and the second electrode 72 through the conductive structure 50 and the output detection terminal 90, which may effectively increase the detection positions of the thin-film transistor 70 and improve the detection efficiency.

It should be noted that the embodiment shown in FIG. 1 only schematically shows that the cross-section of the output detection terminal 90 is an L-shaped structure, and may not represent the actual size of the output detection terminal 90. The structure of the output detection terminal 90 may also be other structures that are not limited in this disclosure.

Figure 3:
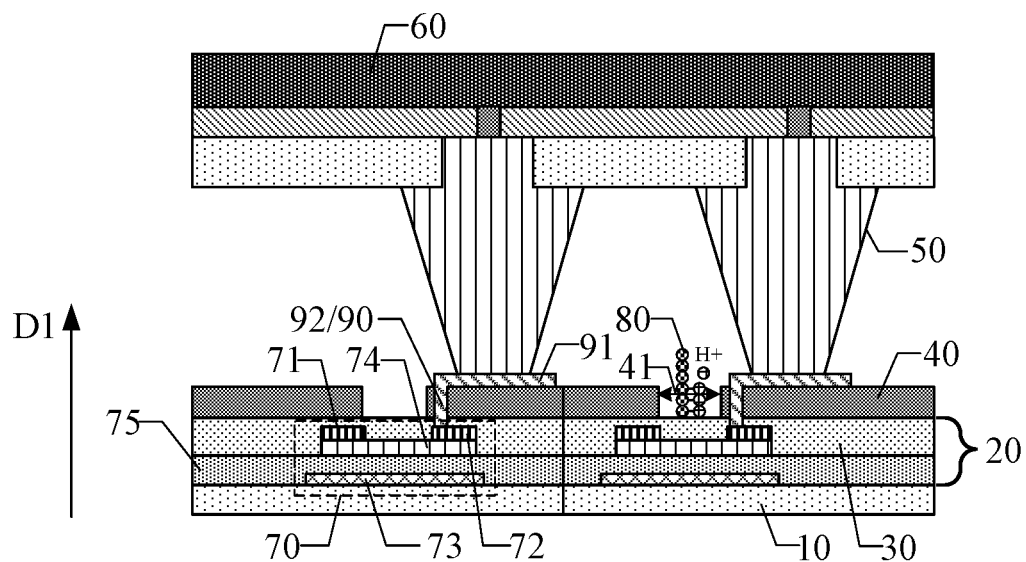
FIG. 3 illustrates a cross-sectional view of another exemplary gene sequencing structure according to various disclosed embodiments of the present disclosure.

FIG. 3 illustrates a cross-sectional view of another exemplary gene sequencing structure consistent with various disclosed embodiments of the present disclosure. As shown in FIG. 3 and referring to FIG. 1, in one embodiment of the present disclosure, the output detection terminal 90 may include a first branch 91 and a second branch 92. The first branch 91 may be located on the side of the micro-hole layer 40 away from the substrate 10, and the first branch 91 may be in contact with the conductive structure 50. The second branch 92 may be located in the micro-hole layer 40, and a portion of the second branch 92 may be located in the ion-sensitive layer 30 and may be in contact with the first electrode 71 or the second electrode 72.

Referring to FIG. 1 and FIG. 3, in one embodiment, the output detection terminal 90 may include two portions: the first branch 91 and the second branch 92. The first branch 91 and the second branch 92 may be a same structure and may be formed at the same time. For example, a contact through-hole may be formed in the micro-hole layer 40 and the ion-sensitive layer 30, the second branch 92 may be formed in the contact through-hole, and the second branch 92 may be electrically in contact with the first electrode 71 or the second electrode 72. The first branch 91 may be located on the side of the micro-hole layer 40 away from the substrate 10, and the first branch 91 may be electrically connected to the conductive structure 50. In such an embodiment, the second branch 92 may be electrically connected with the second electrode 72. In another embodiment, as shown in FIG. 1, a portion of the first branch 91 may be formed in the through-hole 41, and a contact through-hole may not need to be formed in the micro-hole layer 40, and the fabrication process may be simplified. In some embodiments, as shown in FIG. 3, the contact through-hole may pass through the ion-sensitive layer 30. Under such a configuration, the contact through-hole may need to be formed in the ion-sensitive layer 30. In this embodiment, through the first branch 91 and the second branch 92 of the detection terminal 90, the conductive structure 50 and the detection chip 60 may be arranged on the side of the thin-film transistor array layer 20 away from the substrate 10. On the one hand, it may effectively save the space on the side of the substrate 10 away from the array layer 20 of the thin-film transistor 70. On the other hand, it may also effectively reduce the manufacturing cost of the detection chip 60.

Figure 4:
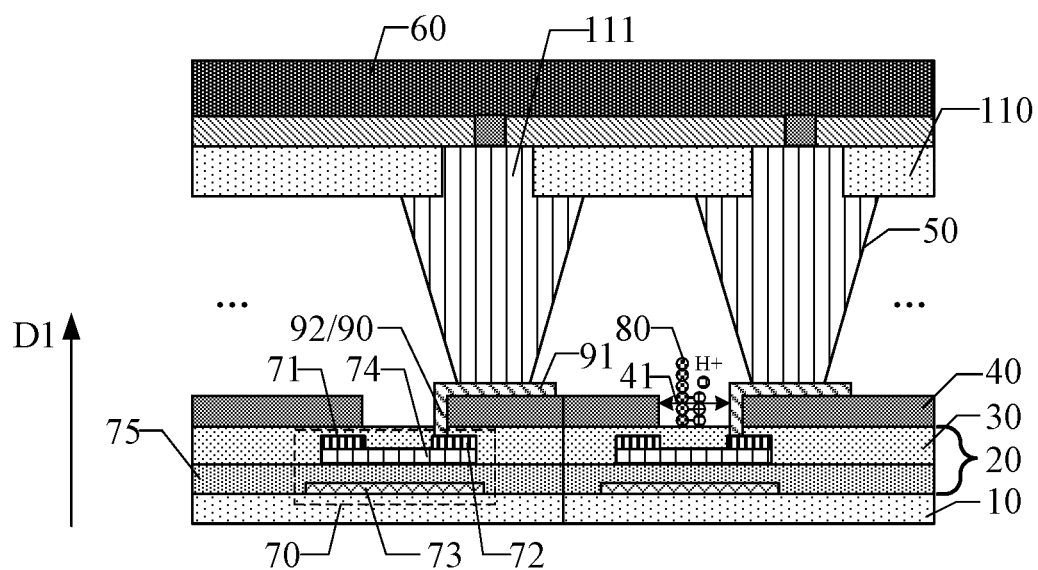
FIG. 4 illustrates a cross-sectional view of another exemplary gene sequencing structure according to various disclosed embodiments of the present disclosure.

FIG. 4 illustrates a cross-sectional view of another exemplary gene sequencing structure according to various disclosed embodiments of the present disclosure. As shown in FIG. 4, in one embodiment of the present disclosure, the gene sequencing structure 100 may further includes a counter substrate 110 located on the side of the conductive structure 50 away from the substrate 10.

The detection chip 60 may be located on the side of the counter substrate 110 away from the conductive structure 50. The counter substrate 110 may include a plurality of conductive hole structures 111 which may be conductive, and the conductive hole structures 111 may be electrically connected to the conductive structure 50. The detection chip 60 may be electrically connected to the conductive hole structures 111 through the first signal wirings 112.

Referring to FIG. 4, the gene sequencing structure 100 in this embodiment may also include the counter substrate 110. In one embodiment, the counter substrate 110 may be a glass substrate, a PCB substrate, or an encapsulation layer, etc. The counter substrate 110 may be located on the side of the conductive structure 50 away from the substrate 10. The counter substrate 110 may be disposed opposite to the substrate 10. The thin-film transistor array layer 20, the ion-sensitive layer 30, the micro-hole layer 40, and the conductive structure 50 may all be located between the counter substrate 110 and the substrate 10. In one embodiment, the detection chip 60 may be located on the side of the counter substrate 110 away from the conductive structure 50, and the plurality of conductive hole structures 111 may be formed in the counter substrate 110. For example, holes may be formed in the counter substrate 110, and a conductive material may be injected into the holes to electrically connect the detection chip 60 and the conductive structure 50. In one embodiment, the conductive material injected into the holes may be made of a same material as the conductive structure 50.

The side of the conductive hole structures 111 adjacent to the substrate 10 may be electrically connected to the conductive structure 50, and the side of the conductive hole structures 111 away from the substrate 10 may be electrically connected to the detection chip 60 through the first signal wiring 112. In such a manner, the detection chip 60 and the conductive structure 50 may be electrically connected; and the detection chip 60 may detect the current change between the first electrode 71 and the second electrode 72. Further, the counter substrate 110 may be in the form of a jig and integrated in the external machine; and may not be used as a consumable, the production cost may be effectively reduced.

It should be noted that the embodiment shown in FIG. 4 only schematically shows the structural diagram of the conductive hole structures 111, and may not represent the actual size of the conductive hole structures 111.

Further, referring to FIG. 4, in another embodiment of the present disclosure, the gene sequencing structure may further include an encapsulation structure 120. The encapsulation structure 120 may be located on the side surface of the stacked structure having the substrate 10, the thin-film transistor array layer 20, the ion-sensitive layer 30, and the micro-hole layer 40, the conductive structure 50 and the opposite substrate 110.

Referring to FIG. 4, the gene sequencing structure 100 in this embodiment may also include the encapsulation structure 120. The encapsulation structure 120 may encapsulate the stacked structure having the substrate 10, the thin-film transistor array layer 20, the ion-sensitive layer 30, the micro-hole layer 40, the conductive structure 50 and the counter substrate 110. In one embodiment, the encapsulation structure 120 may be located on the side surface of the above stacked structure. Along the direction D2 parallel to the substrate 10, the detection chip 60 may be bound to the side of the counter substrate 110 away from the substrate 10. Such a configure may effectively save the space on the side of the substrate 10 away from the counter substrate 110.

It should be noted that the embodiment shown in FIG. 4 only schematically shows a schematic diagram of the encapsulation structure 120 encapsulating two gene sequencing structures. In some embodiments, the encapsulation structure 120 may also encapsulate multiple gene sequencing structures, which is not limited in this disclosure.

Figure 5:
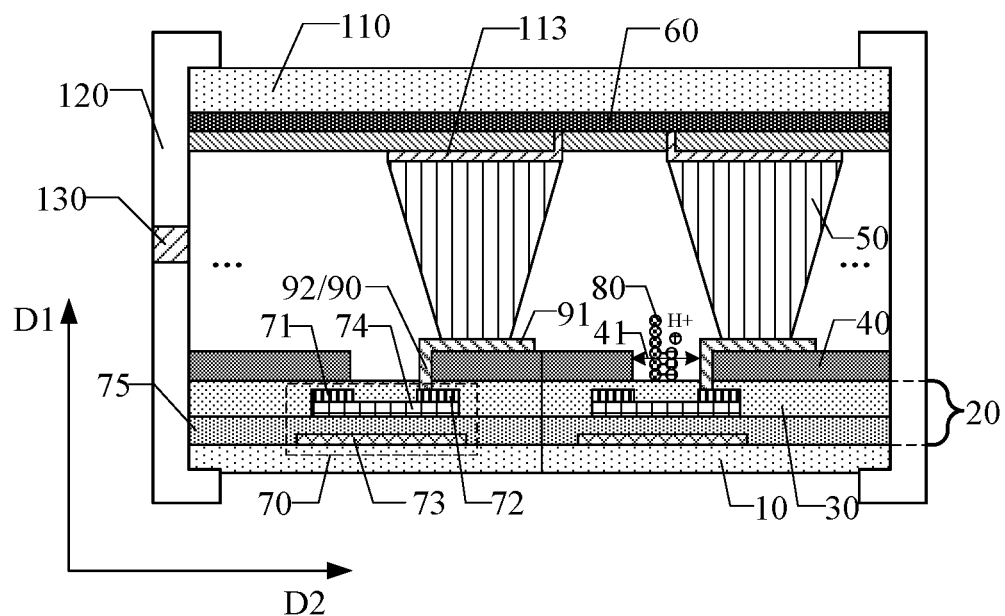
FIG. 5 illustrates a cross-sectional view of another exemplary gene sequencing structure according to various disclosed embodiments of the present disclosure.
Figure 6:
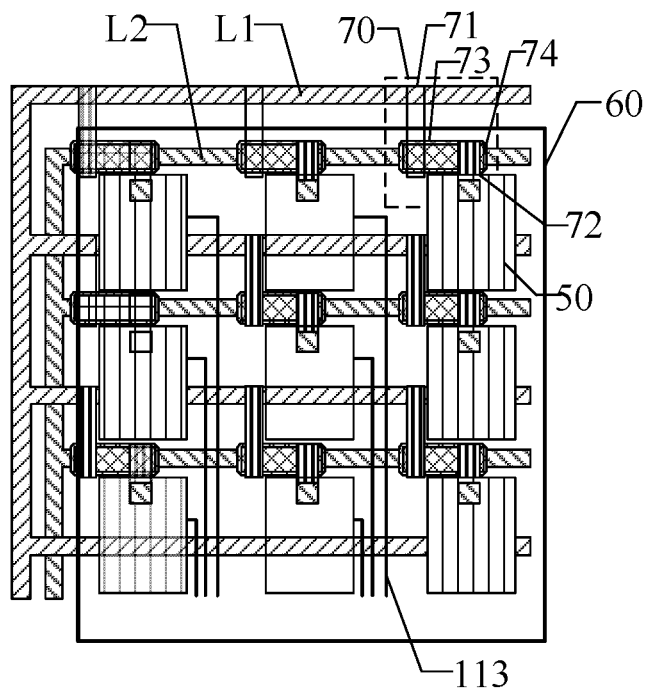
FIG. 6 illustrates a cross-sectional view of another exemplary gene sequencing structure according to various disclosed embodiments of the present disclosure.

FIG. 5 illustrates a cross-sectional view of another exemplary gene sequencing structure accordingly to various disclosed embodiments of the present disclosure, and FIG. 6 shows a schematic top view of another exemplary gene sequencing structure according to various disclosed embodiments of the present disclosure. As shown in FIG. 5 and FIG. 6, in one embodiment of the present disclosure, the gene sequencing structure 100 may also include a counter substrate 110. The counter substrate 110 may be located on the side of the conductive structure 50 away from the substrate 10.

The detection chip 60 may be located on the side of the counter substrate 110 adjacent to the conductive structure 50. The detection chip 60 and the conductive structure 50 may be electrically connected through the second signal wiring 113.

Referring to FIGS. 5-6, the gene sequencing structure 100 in this embodiment may include the counter substrate 110. The counter substrate 110 may be a glass substrate 10, a PCB substrate 10, or an encapsulation structure, etc. The counter substrate 110 may be located on the side of the conductive structure 50 away from the substrate 10. In one embodiment, the conductive structure 50 may be fabricated in the counter substrate 110. The counter substrate 110 may be arranged opposite to the substrate 10. The thin-film transistor array layer 20, the ion-sensitive layer 30, the micro-hole layer 40, the conductive structure 50, and the detection chip 60 may all be disposed between the counter substrate 110 and the substrate 10. The detection chip 60 may be electrically connected to the conductive structure 50 through the second signal wiring 113 to achieve the electrical connection between the detection chip 60 and the conductive structure 50. The detection chip 60 may detect the current change between the first electrode 71 and the second electrode 72. Further, the counter substrate 110 may be in the form of a jig, may be integrated in an external machine, and may not be used as a consumable. Accordingly, the cost may be reduced.

Figure 7:
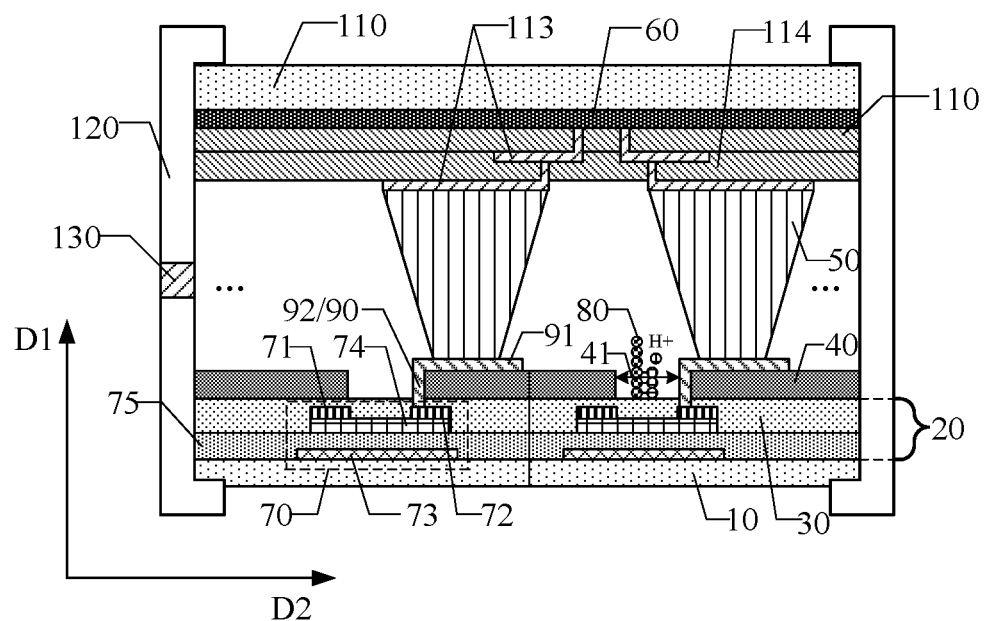
FIG. 7 illustrates a cross-sectional view of an exemplary gene sequencing device according to various disclosed embodiments of the present disclosure.

FIG. 7 illustrates a cross-sectional view of anther exemplary gene sequencing structure according to various disclosed embodiments of the present disclosure. As shown in FIG. 7, in one embodiment of the present disclosure, a first insulation layer 114 may be disposed among a plurality of second signal wirings 113.

Referring to FIG. 7, in this embodiment, in view of the large number of second signal wirings 113, the plurality of second signal wirings 113 may be disposed in different layers. The first insulation layer 114 may be disposed between the detection chip 60 and the second signal wirings 113 of the conductive structure 50, and the second signal wirings 113 in different layers may be electrically connected through vias. In such a configuration, the electrical connection between detection chip 60 and the conductive structure 50 may be achieved, while the concentrated wiring of the second signal wirings 113 may be avoided to avoid a poor load.

It should be noted that the embodiment shown in FIG. 7 only schematically shows a structure diagram provided with two layers of second signal wirings 113, multiple layers of second signal wirings 113 may also be provided, and an insulation layer may be disposed among the multiple layers of second signal wirings 113, which is not limited in the present disclosure.

Further referring to FIG. 5 and FIG. 7, in anther embodiment of the present disclosure, the gene sequencing structure 100 may further include the encapsulation structure 120. The encapsulation structure 120 may be disposed on the side surfaces of a stacked structure having the substrate 10, the thin-film transistor array layer 20, the ion-sensitive layer 30, the micro-hole layer 40, the conductive structure 50, the detection chip 60 and the counter substrate 110.

Referring to FIG. 5 and FIG. 7, in the gene sequencing structure 100 in this embodiment, the encapsulation structure 120 may encapsulate the stacked structure including the substrate 10, the thin-film transistor array layer 20, the ion-sensitive layer 30, the micro-hole layer 40, the conductive structure 50, the detection chip 60 and the counter substrate 110. In one embodiment, the encapsulation structure 120 may be located on the side surface of the stacked structure and the side surface D2 parallel to the substrate 100. In such a manner, the detection chip 60 may be bound to the side of the counter substrate 110 away from the substrate 10. Accordingly, the space on the side of the substrate 10 away from the counter substrate 110 may be effectively saved.

Further, referring to FIG. 4 to FIG. 7, in one embodiment of the present disclosure, the encapsulation structure 120 may include a plurality of openings 130.

Referring to FIGS. 4-7, the encapsulation structure 120 in this embodiment may include a plurality of openings 130. The openings 130 may be located at any position of the encapsulation structure 120. The openings 130 may be used to inject a single-stranded nucleic acid into the through-hole 41 of the micro-hole layer 40, and it may also be used to inject pairing bases into the through-hole 41, and it may also discharge the unnecessary solution in the through-hole 41. For example, the opening 130 may be used for injecting or discharging a solution into the through-hole 41 of the micro-hole layer 40.

It should be noted that the embodiments shown in FIGS. 4 to 7 only schematically show one position where the opening is located. The opening may also be located at other positions, which is not limited in the present disclosure.

Further, referring to FIG. 1, in embodiment of the present disclosure, the diameter of the through-hole 41 may be in a range of approximately 3 μm-6 μm.

Referring to FIG. 1, the diameter of the through-hole 41 in this embodiment may be in a range of approximately 3 μm-6 μm. In one embodiment, the diameter of the through-hole 41 may also be 4 μm or 5 μm. If the diameter of the through-hole 41 is greater than 6 μm, it may affect the number of through-holes 41. If the diameter of the through-hole 41 is smaller than 3 μm, it may be difficult to achieve by using the panel technology. By limiting the diameter of the through-holes 41, there may be more detection positions integrated in the gene sequencing structure 100. Accordingly, the detection efficiency may be improved.

It should be noted that the embodiment shown in FIG. 1 only schematically shows the structural diagram of the through-holes 41, and may not represent the actual size of the through-holes 41.

Further, referring to FIG. 1, in another embodiment of the present disclosure, along the direction D1 perpendicular to the substrate 10, the height of the conductive structure 50 may be in a range of approximately 3 μm-5 μm.

Referring to FIG. 1, in such an embodiment, along the direction D1 perpendicular to the substrate 100, the height of the conductive structure 50 may be in a range of approximately 3 μm-5 μm. In one embodiment, the height of the conductive structure 50 may be approximately 4 μm. In such a case, the substrate 10 may be a glass substrate. In such a configuration, the patterning accuracy of the conductive structure 50 may be higher, which may facilitate the realization of the requirement for the detection positions of the high-density thin-film transistor 70s in the present disclosure.

It should be noted that the embodiment shown in FIG. 1 only schematically shows a schematic structural diagram of the conductive structure 50 and may not represent the actual size of the conductive structure 50.

In one embodiment of the present application, the material of the conductive structure 50 may be electroplated copper.

For example, the conductive structure 50 in this embodiment may be made of electroplated copper. When the conductive structure 50 is electroplated with a height of 3 μm to 5 μm in the direction D1 perpendicular to the substrate 10, a highly accurate conductive structure 50 may be realized. At this time, the substrate 10 may be a glass substrate. When the conductive structure 50 is electroplated with copper with a height of 5 μm to 50 μm in the direction D1 perpendicular to the substrate 100, the requirements for the production accuracy may be relatively low. At this time, the substrate 10 may be a PCB substrate, the warpage of the substrate 10 may be avoided.

Further, referring to FIG. 1, in another embodiment of the present disclosure, the thin-film transistor 70 may be a bottom-gated structure.

Referring to FIG. 1, the thin-film transistor 70 in this embodiment may be a bottom-gated structure. It may be understandable that the third electrode 73 in this embodiment may be the gate of the thin-film transistor 70. For example, the gate may be located on the semiconductor layer 74 adjacent to the substrate 10. In such a configuration, the potential change generated above the thin-film transistor 70 may not be shielded by the third electrode 73, i.e., the gate, but the conductivity of the semiconductor layer 74 may be changed by the ion-sensitive layer 30.

In one embodiment of the present disclosure, the material of the ion-sensitive layer 30 layer may be silicon nitride, or silicon oxide, etc.

The material of the ion-sensitive layer 30 in this embodiment may be silicon nitride or silicon oxide. The ion-sensitive layer 30 may be used to sense changes in ions and to sense the occurrence of the base pairing. The ion-sensitive layer 30 may be formed by hydrogen-ion-sensitive material, or the ion-sensitive material a voltage of which may be changed by the ions generated in the base pairing. Silicon nitride or silicon oxide may achieve the required functions of the ion-sensitive layer 30.

Figure 8:
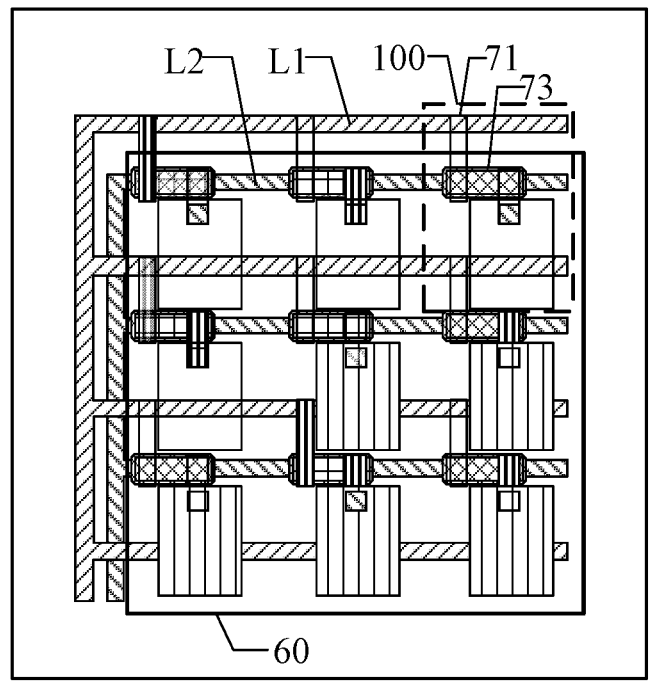
FIG. 8 illustrates a top view of an exemplary gene sequencing device according to various disclosed embodiments of the present disclosure.

The present disclosure also provides a gene sequencing device. FIG. 8 illustrates a cross-sectional view of an exemplary gene sequencing device according to various disclosed embodiments of the present disclosure, and FIG. 9 illustrates a top view of an exemplary gene sequencing device according to various disclosed embodiments of the present disclosure.

Figure 9:
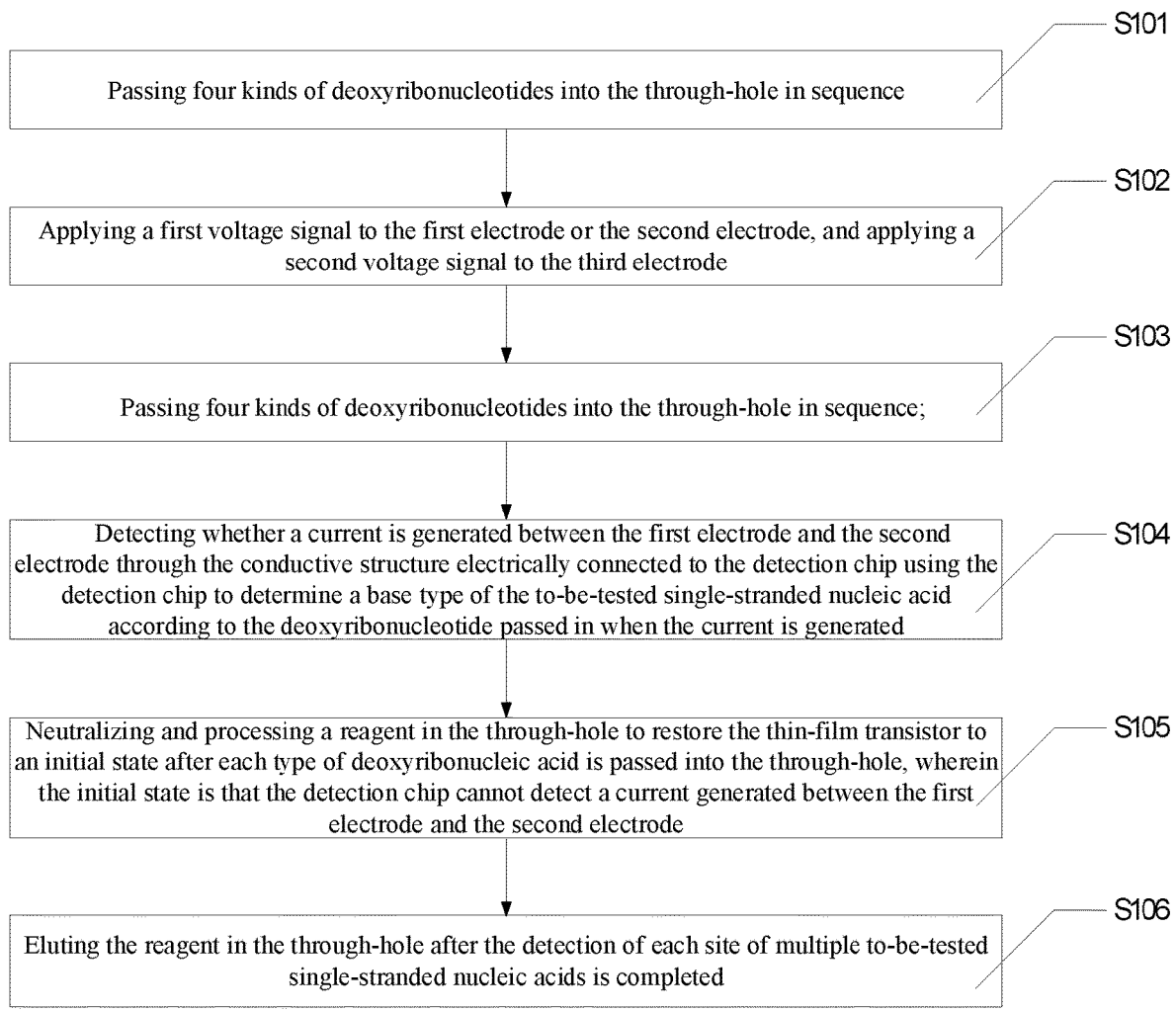
FIG. 9 illustrates a flow chart of an exemplary gene sequencing method according to various disclosed embodiments of the present disclosure.

As shown in FIG. 8 and FIG. 9, the gene sequencing device 200 may include a plurality of gene sequencing structures 100. The gene sequencing structure 100 may be the gene sequencing structure provided by any embodiment of the present disclosure. In the gene sequencing device 200 of the present disclosure, a plurality of gene sequencing structures 100 may be arranged in an array.

Referring to FIG. 8 and FIG. 9, the plurality of gene sequencing structures 100 may be arranged as an array or may be arranged uniformly. They may also be arranged in other ways, which are not limited in this application. In different gene sequencing structures 200, all the first electrodes 71 or the second electrodes 72 may input a same first voltage signal through the first metal wiring L1, and all the third electrodes 73 may input a same second voltage signal through the second metal wiring L2. The connection lines of the first electrodes 71 or the second electrodes 72 in the gene sequencing structures 100 located in a same row or a same column may be connected in parallel. The connection lines of the third electrodes 73 in the gene sequencing structures 100 located in a same row or a same column may be connected in parallel. In this embodiment, the first electrodes 71 of the gene sequencing structures 100 located in the same row may be connected in parallel, and the third electrodes 73 of the gene sequencing structures 100 located the same row may be connected in parallel. On the one hand, the gene sequencing structures 100 arranged in the array may be able to improve the efficiency of the gene sequencing. On the other hand, the gene sequencing structures 100 may be used to sense whether the bases on the to-be-tested nucleic acid single strand 80 are paired, the gene sequencing may be simple, and the cost of the gene sequencing may be effectively reduced.

Figure 10:
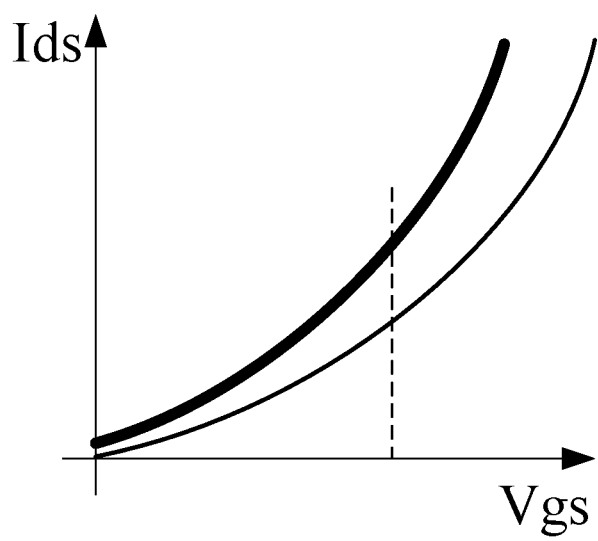
FIG. 10 illustrates an exemplary variation diagram of a current between a first electrode and a second electrode according to various disclosed embodiments of the present disclosure.

Further, the present disclosure provides a gene sequencing method. FIG. 10 illustrates a flow chart of an exemplary gene sequencing method according to various disclosed embodiment of the present disclosure. FIG. 11 is a variation curve of the current between the electrode and the second electrode according to various disclosed embodiments of the present disclosure. The gene sequencing method may use the present disclosed gene sequence structure and gene sequencing device to perform a gene sequencing. As shown in FIGS. 10-11, and referring to FIG. 1, the gene sequencing method may include:

- in S101: placing a to-be-tested single-stranded nucleic acid 80 in the through-hole 41 by contacting with the ion-sensitive layer 30;
- in S102: applying a first voltage signal to the first electrode 71 or the second electrode 72, and applying a second voltage signal to the third electrode 73;
- in S103: passing four kinds of deoxyribonucleotides into the through-hole 41 in sequence;
- in S104: detecting whether a current is generated between the first electrode 71 and the second electrode 72 through the conductive structure 50 electrically connected to the detection chip 60 using the detection chip 60 to determine the base type of the to-be-tested single-stranded nucleic acid 80 according to the deoxyribonucleotide introduced therein as the current is generated;
- in S105: neutralizing and processing the reagent in the through-hole 41 to restore the thin-film transistor 70 to the initial state after each type of deoxyribonucleic acid is passed into the through-hole 41, wherein the initial state is that the detection chip 60 cannot detect the current generated between the first electrode 71 and the second electrode 72; and
- in S106: eluting the reagent in the through-hole 41 after the detection of each site of multiple to-be-tested single-stranded nucleic acids 80 is completed.

Referring to FIG. 10 and FIG. 11 and referring to FIG. 1 and FIG. 2, the present disclosed gene sequencing method may utilize the present disclosed gene sequencing structure. Thus, the gene sequencing method may be relatively simple, and the cost of gene sequencing method may be reduced.

In S101 of the gene sequencing method, different to-be-tested single-stranded nucleic acids 80 may be loaded into different through-holes 41 through the openings 130 on the sidewalls of the encapsulation structure 120, and the to-be-tested single-stranded nucleic acids 80 may be in touch with the ion-sensitive layer 30 exposed by the through-holes 41.

In S102, a first voltage signal may be applied to the first electrode 71, or may be applied to the second electrode 72, and a second voltage signal may be applied to the third electrode 73. The first voltage signal and the second voltage signal may be same or different. In one embodiment, the first voltage signal may be applied to the first electrode 71 through the first metal wiring L1, and the second voltage signal may be applied to the third electrode 73 through the second metal wiring L2.

In S103, an adenine may be injected into different through-holes 41 through the openings 130 on the sidewalls of the encapsulation structure 120. If the first site of the single-stranded nucleic acid 80 in the through-hole 41 is paired, hydrogen ions may be released, which may cause the potential on the semiconductor layer 74 to change, and whether the current between the first electrode 71 and the second electrode 72 changes may be detected by the detection chip 60. If the current changes, the pairing is successful, and it may be determined that the base pairing is successful. The type of the base of the first site of the single-stranded nucleic acid 80 in the through-hole 41 may be determined as T thymine. Then, the T thymine may be injected into the through-hole 41 to further determine the base of the single-stranded nucleic acid 80 in the through-hole 41 to the A adenine. Sequentially, the C cytosine and G guanine may be injected into the through-holes 41 until the bases at the first sites of the single-stranded nucleic acids 80 in all the through-holes 41 match. At this time, the reagent in the through-hole 41 may be eluted to prepare for the gene detection of the single-stranded nucleic acid 80 at the second site in the through-hole 41. The specific detection method may be same as that of the first site.

In S104, in the above steps, when the deoxyribonucleotides passing through the through-hole 41 successfully pairs with the bases of the to-be-tested single-stranded nucleic acids 80, the detection chip 60 may detect whether a current generated between the first electrode 71 and the first electrode 71 through the conductive structure 50 changes. If the current generated between the first electrode 71 and the second electrode 72 changes, the base pairing may be successful. The type of the base of the to-be-tested single-stranded nucleic acid 80 may be determined according to the type of the deoxyribonucleotide passed in.

In S105, in the above steps, after each type of deoxyribonucleotide is passed into the through-hole 41, the reagent in the through-hole 41 may need to be neutralized to restore the thin-film transistor 70 to the initial state. The initial state of the thin-film transistor 70 may be that the detection chip 60 may not detect the current generated between the first electrode 71 and the second electrode 72. When the bases of the to-be-tested single-stranded nucleic acid 80 are paired, the concentration of hydrogen ions in the through-hole 41 may change. If it is not processed in time, it may affect the concentration of hydrogen ions generated after the next deoxyribonucleotide passes into the through-hole 41 and pairs with the with the to-be-tested single-stranded nucleic acid 80 and may further affect the current change between the first electrode 71 and the second electrode 72. Accordingly, the accuracy of this pairing detection may be affected.

Therefore, after each pairing happens on the base of the to-be-tested single-stranded nucleic acid 80, the reagent in the through-hole 41 may need to be neutralized to avoid causing the subsequent errors.

In S106, in the above steps, the single-stranded nucleic acid 80 in the through-hole 41 includes a plurality of site bases. After the detection of the first sites of the single-stranded nucleic acids 80 in all the through-holes 41 is completed, the solution in the through-holes 41 may need to be eluted to ensure that the reagent in the through-holes 41 may return to the original state, and may not affect the detection of the second sites of the single stranded nucleic acids 80 in all the through-holes 41.

In one embodiment, the first voltage signal may be applied to the first electrode 71 through the first metal wiring L1, and the second voltage signal may be applied to the second electrode 72 through the second metal wiring L2. A certain current may be generated between the first electrode 71 and the second electrode 72 and the thin-film transistor 70 may be operated in the linear region. On this basis, after the bases of the to-be-tested single-stranded nucleic acids 80 in the through-holes 41 are paired, a potential change may be generated above the thin-film transistor 70. The conductivity of the semiconductor layer 74 may be further changed to make the current change between the first electrode 71 and the second electrode 72 more obvious.

Referring to the current change between the first electrode 71 and the second electrode 72 shown in FIG. 11, the thick solid line illustrates the successful base pairing on the tested single-stranded nucleic acid 80, and the thin solid line illustrates the unsuccessful base pairing on the tested single-stranded nucleic acid 80. The abscissa in FIG. 11 is the voltage of the semiconductor layer 74, the ordinate is the current between the first electrode 71 and the second electrode 72. Through the above sequencing method, the detection of the gene sequence may be more convenient and efficient. Further, in this embodiment, after all the bases of the to-be-tested single-stranded nucleic acids 80 are tested, the reagent in the through-hole 41 may be eluted, which may ensure the accuracy of the gene sequencing at the next site of the single-stranded nucleic acid 80.

In one embodiment of the present disclosure, neutralizing the reagent in the through-holes 41 may include following steps.

After the base of the to-be-tested single-stranded nucleic acid 80 in the through-hole 41 is paired with the deoxyribonucleotides introduced into the through-hole 41, a phosphate buffer solution may be injected into the through-hole 41 through the opening 130 to neutralize the hydrogen ions in the through-hole 41 to restore the hydrogen ion concentration index in the through-hole 41 to the value before the introduction of deoxyribonucleotides.

In one embodiment, the phosphate buffer solution may be used to neutralize the reagent in the through-hole 41 such that the concentration index of hydrogen ions in the through-hole 41 may not affect the continuation of the pairing of the bases on the to-be-tested single-stranded nucleic acid, and the accuracy of gene sequencing results may be ensured.

It can be seen from the above embodiments that the present disclosed gene sequencing structure, gene sequencing device and gene sequencing method may have the following beneficial effects.

The gene sequencing structure, gene sequencing device and gene sequencing method provided by the present disclosure may be provided with a substrate, a thin-film transistor array layer, an ion-sensitive layer, a micro-hole layer, a conductive structure, and a detection chip. The successful base pairing may cause a change in the potential above the thin-film transistor. The conductivity of the semiconductor layer in the thin-film transistor may be used to generate a current between the first electrode and the second electrode. The change in the current may be detected by the detection chip to detect the sequence of the gene. The base of the to-be-detected single-stranded nucleic acid may not require a fluorescent labeling, laser light source and optical system. Further, the signal control of the third electrode is added in this disclosure to make the thin-film transistor being operated in the linear region. Accordingly, the current change detection between the first electrode and the second electrode may be more obvious. Further, the present disclosure may also introduce a conductive structure, which may effectively increase the detection positions of the thin-film transistor, and may effectively improve the experimental efficiency. On the other hand, the detection chip may be arranged on the side of the conductive structure away from the substrate, which may effectively save the space on the side of the substrate.

The above are only specific embodiments of the present disclosure, but the protection scope of the present disclosure is not limited thereto. Any person skilled in the art can easily think of various equivalent modifications or changes within the technical scope disclosed in the present disclosure. Equivalent modifications or replacements should all be covered within the protection scope of the present disclosure. Therefore, the protection scope of the present disclosure should be subject to the protection scope of the claims.

What is claimed is:

1. A gene sequencing structure, comprising:
   a substrate;
   a thin-film transistor array layer, located on a side of the substrate, wherein the thin-film transistor array layer includes a plurality of thin-film transistors, each of the plurality of thin-film transistors includes a first electrode, a second electrode, a third electrode, and a semiconductor layer, the first electrode and the second electrode are spaced apart and located in a same layer, the semiconductor layer is located on a side of the first electrode and the second electrode adjacent to the substrate, the semiconductor layer at least partially overlaps the first electrode and the second electrode, respectively, the semiconductor layer at least partially overlaps the third electrode, and an insulation layer is disposed between the semiconductor layer and the third electrode;
   an ion-sensitive layer, located on a side of the semiconductor layer away from the substrate;
   a micro-hole layer, located on a side of the ion-sensitive layer away from the substrate, wherein the micro-hole layer includes a through-hole, the through-hole passes through the micro-hole layer in a direction perpendicular to the substrate, the through-hole at least partially overlaps the semiconductor layer, and the through-hole is used for receiving a to-be-tested single-stranded nucleic acid;
   a conductive structure, located on a side of the micro-hole layer away from the substrate, wherein the conductive structure is electrically connected to the first electrode or the second electrode; and
   a detection chip, located on a side of the conductive structure away from the substrate, and electrically connected to the conductive structure.

2. The gene sequencing structure according to claim 1, further comprising:
   an output detection terminal, wherein:
the output detection terminal is disposed between the conductive structure and one of the first electrode and the second electrode; and
the conductive structure is electrically connected to one of the first electrode and the second electrode through the output detection terminal.

3. The gene sequencing structure according to claim 2, wherein:
the output detection terminal includes a first branch and a second branch;
the first branch is located on a side of the micro-hole layer away from the substrate and the first branch is in contact with the conductive structure; and
the second branch passes through the micro-hole layer, is partially located on the ion-sensitive layer, and is in contact with the first electrode or the second electrode.

4. The gene sequencing structure according to claim 1, further comprising:
a counter substrate, disposed on a side of the conductive structure away from the substrate,
wherein:
the detection chip is located on a side of the counter substrate away from the conductive structure;
the counter substrate includes a plurality of conductive hole structures;
the plurality of conductive hole structures are electrically connected to the conductive structure; and
the detection chip is electrically connected with the plurality of conductive hole structures through first signal wirings.

5. The gene sequencing structure according to claim 4, further comprising:
an encapsulation structure, located on side surfaces of a stacked structure having the substrate, the thin-film transistor array layer, the ion-sensitive layer, the micro-hole layer, the conductive structure, and the counter substrate.

6. The gene sequencing structure according to claim 1, further comprising:
a counter substrate, located on a side of the conductive structure away from the substrate;
wherein:
the detection chip is located on a side of the counter substrate adjacent to the conductive structure; and
the detection chip and the conductive structure are electrically connected through a plurality of second signal wirings.

7. The gene sequencing structure according to claim 6, wherein:
the plurality of second signal wirings are disposed in a first insulation layer.

8. The gene sequencing structure according to claim 6, further comprising:
an encapsulation structure, located on side surfaces of a stacked structure having the substrate, the thin-film transistor array layer, the ion-sensitive layer, the micro-hole layer, the conductive structure, the detection chip, and the counter substrate.

9. The gene sequencing structure according to claim 8, wherein the encapsulation structure comprises:
a plurality of openings.

10. The gene sequencing structure according to claim 1, wherein:
a diameter of the through-hole is in a range of approximately 3 µm-6 µm.

11. The gene sequencing structure according to claim 1, wherein:
in a direction perpendicular to the substrate, a height of the conductive structure is in a range of approximately 3 µm-5 µm.

12. The gene sequencing structure according to claim 1, wherein:
the conductive structure is made of electroplated copper.

13. The gene sequencing structure according to claim 1, wherein:
the thin-film transistor is a bottom-gated structure.

14. The gene sequencing structure according to claim 1, wherein:
the ion-sensitive layer is made of one of silicon nitride and silicon oxide.

15. A gene sequencing device, comprising:
a plurality of gene sequencing structures,
wherein each of the plurality of gene sequencing structures includes:
a substrate;
a thin-film transistor array layer, located on a side of the substrate, wherein the thin-film transistor array layer includes a plurality of thin-film transistors, each of the plurality of thin-film transistors includes a first electrode, a second electrode, a third electrode, and a semiconductor layer, the first electrode and the second electrode are spaced apart and located in a same layer, the semiconductor layer is located on a side of the first electrode and the second electrode adjacent to the substrate, the semiconductor layer at least partially overlaps the first electrode and the second electrode, respectively, the semiconductor layer at least partially overlaps the third electrode, and an insulation layer is disposed between the semiconductor layer and the third electrode;
an ion-sensitive layer, located on a side of the semiconductor layer away from the substrate;
a microporous layer, located on a side of the ion-sensitive layer away from the substrate, wherein the micro-hole layer includes a through-hole, the through-hole passes through the micro-hole layer in a direction perpendicular to the substrate, the through-hole at least partially overlaps the semiconductor layer, and the through-hole is used for placing a to-be-tested single-stranded nucleic acid inside;
a conductive structure, located on a side of the micro-hole layer away from the substrate, wherein the conductive structure is electrically connected to the first electrode or the second electrode; and
a detection chip, located on a side of the conductive structure away from the substrate, and electrically connected to the conductive structure.

16. A gene sequencing method, comprising:
providing a gene sequencing structure, including:
a substrate;
a thin-film transistor array layer, located on a side of the substrate, wherein the thin-film transistor array layer includes a plurality of thin-film transistors, each of the plurality of thin-film transistors includes a first electrode, a second electrode, a third electrode, and a semiconductor layer, the first electrode and the second electrode are spaced apart and located in a same layer, the semiconductor layer is located on a side of the first electrode and the second electrode adjacent to the substrate, the semiconductor layer at least partially overlaps the first electrode and the second electrode, respectively, the semiconductor layer at least partially overlaps the third electrode, and an insulation layer is disposed between the semiconductor layer and the third electrode;

an ion-sensitive layer, located on a side of the semiconductor layer away from the substrate;

a micro-hole layer, located on a side of the ion-sensitive layer away from the substrate, wherein the micro-hole layer includes a through-hole, the through-hole passes through the micro-hole layer in a direction perpendicular to the substrate, the through-hole at least partially overlaps the semiconductor layer, and the through-hole is used for placing a to-be-tested single-stranded nucleic acid inside;

a conductive structure, located on a side of the micro-hole layer away from the substrate, wherein the conductive structure is electrically connected to the first electrode or the second electrode; and a detection chip, located on a side of the conductive structure away from the substrate, and electrically connected to the conductive structure;

placing the to-be-tested single-stranded nucleic acid in the through-hole by contacting with the ion-sensitive layer;

applying a first voltage signal to the first electrode or the second electrode, and applying a second voltage signal to the third electrode;

passing four kinds of deoxyribonucleotides into the through-hole in sequence;

detecting whether a current is generated between the first electrode and the second electrode through the conductive structure electrically connected to the detection chip using the detection chip to determine a base type of the to-be-tested single-stranded nucleic acid according to the deoxyribonucleotide introduced therein as the current is generated;

neutralizing and processing a reagent in the through-hole to restore the thin-film transistor to an initial state after each type of deoxyribonucleotide is passed into the through-hole, wherein the initial state is that the detection chip is unable to detect a current generated between the first electrode and the second electrode; and eluting the reagent in the through-hole after the detection of each site of multiple to-be-tested single-stranded nucleic acids is completed.

17. The gene sequencing method according to claim 16, wherein neutralizing and processing the reagent in the through-hole comprises:

injecting a phosphate buffer solution into the through-hole through the opening to neutralize hydrogen ions in the through-hole to restore a hydrogen ion concentration index in the through-hole to a value before an introduction of deoxyribonucleotides after a base of the to-be-tested single-stranded nucleic acid in the through-hole is paired with the deoxyribonucleotide introduced into the through-hole.

* * * * *